(12) United States Patent
Zong

(10) Patent No.: US 6,519,611 B1
(45) Date of Patent: Feb. 11, 2003

(54) METHOD AND APPARATUS FOR COMPUTER AUTOMATED DETECTION OF PROTEIN AND NUCLEIC ACID TARGETS OF A CHEMICAL COMPOUND

(75) Inventor: Chen Yu Zong, Singapore (SG)

(73) Assignee: National University of Singapore (SG)

( * ) Notice: Subject to any disclaimer, the term of this patent is extended or adjusted under 35 U.S.C. 154(b) by 244 days.

(21) Appl. No.: 09/655,238

(22) Filed: Sep. 5, 2000

(30) Foreign Application Priority Data

Sep. 6, 1999 (SG) ............................................. 9904404

(51) Int. Cl.$^7$ .............................................. G06F 17/30
(52) U.S. Cl. ................................................... 707/104.1
(58) Field of Search .............................. 707/101, 104.1; 424/188.1, 209.1; 435/5, 6, 7.6, 68.1, 69.7, DIG. 51; 436/518; 514/2, 18, 678; 702/19; 703/11

(56) References Cited

U.S. PATENT DOCUMENTS

| | | | |
|---|---|---|---|
| 6,080,791 A | * | 6/2000 | Bodian et al. ............... 514/678 |
| 6,189,013 B1 | * | 2/2001 | Maslyn et al. ................. 702/20 |
| 6,223,186 B1 | * | 4/2001 | Rigault et al. .................. 435/6 |
| 6,230,102 B1 | * | 5/2001 | Tidor et al. .......... 435/DIG. 51 |

* cited by examiner

Primary Examiner—Diane D. Mizrahi
Assistant Examiner—Apu M Mofiz
(74) Attorney, Agent, or Firm—Knobbe Martens Olson Bear LLP

(57) ABSTRACT

A method and apparatus are disclosed for automated detection of possible protein and nucleic acid targets of a given drug. The advantage of this invention over existing methods is its unique capability of drug target detection. In contrast, existing computer methods are designed for screening multiple chemical compounds to find one or more compounds that can bind to a protein or nucleic acid, and they are not capable of finding drug targets. Potential applications of this method and apparatus include unknown target or secondary target identification for drugs, lead compounds, and natural products. It may also potentially facilitate the prediction of drug side-effect and toxicity based on the analysis of function of identified protein or nucleic acid targets. A ligand-biomolecule inverse-docking algorithm is disclosed to flexibly dock a ligand to multiple entries in a biomolecular cavity database. Docking is accomplished by matching atoms of a ligand in single or multiple conformations to spheres in a sphere cluster representing a cavity in the biomolecule by means of a disclosed vector-vector matching algorithm. The docked structures are subject to conformation optimization for both the ligand and the side-chains of protein or nucleic acid residues around the ligand. A method is also disclosed for computer automated generation of a biomolecular cavity database using entries from protein and nucleic acid 3D structure database. The number of proteins and nucleic acids in this database is comparable to that in Brookhaven Protein Databank (the most popular public domain protein and nucleic acid 3D structure database).

10 Claims, 11 Drawing Sheets

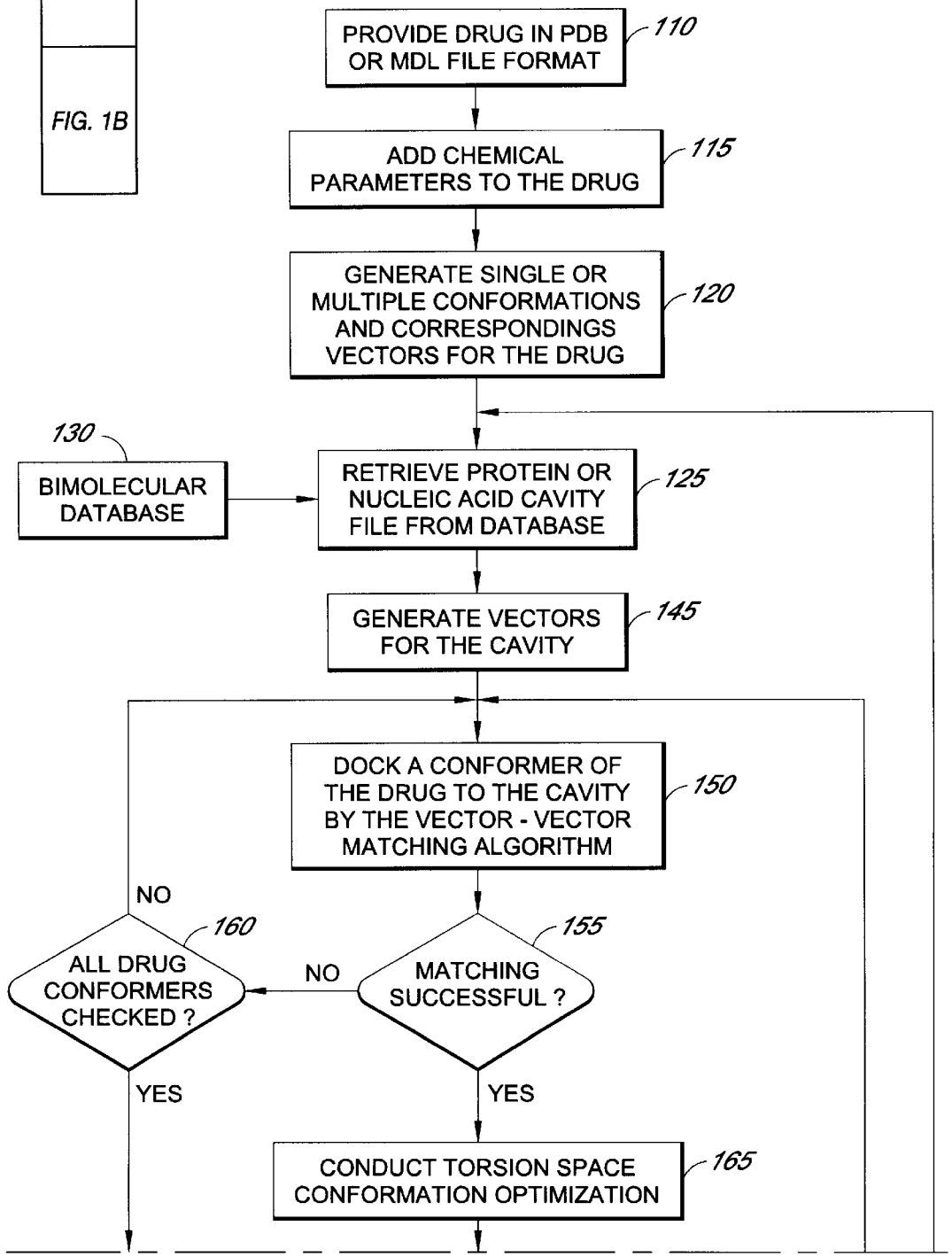

An inhibitor docked into the cavity
of a HIV-1 protease by vector - vector docking algorithm

METHOD AND APPARATUS FOR COMPUTER AUTOMATED DETECTION OF PROTEIN AND NUCLEIC ACID TARGETS OF A CHEMICAL COMPOUND

RELATED APPLICATIONS

This application claims priority under 35 U.S.C. 119 to Singapore Application Number 9904404-2 filed on Sep. 6, 1999.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyrights whatsoever.

BACKGROUND OF THE INVENTION

1. Field of the Invention

This invention relates to methods and apparatus for detecting protein and nucleic acid targets of a drug molecule. Aspects of the invention relate to selecting proteins and nucleic acids from a biomolecular cavity database that a drug can bind to; both geometrically and chemically. This general field is known as "Molecular Modeling" (MM) and "Computer Assisted Molecular Design" (CAMD). When used for pharmaceutical discovery, this field is referred to as "Computer-Aided Drug Design" (CADD).

2. Description of the Related Art and Summary

The Need for a Computer Drug Target Prediction Method

A number of strategies have been proposed and used for rational discovery of new drugs. These include combinatorial chemistry, which is described in "Directed combinatorial chemistry", J. C. Hogan Jr. Nature 384 suppl., 17–19 (1996); high-throughput screening, which is described in "High-throughput screening for drug discovery", J. R. Broach and J. Thorner. Nature 384 suppl., 14–16 (1996).; QSAR, which is described in "Strategies for indirect computer-aided drug Design", Loew G H, Villar H O, Alkorta I, Pharm Res 10, 475–86 (1993); and structure-based molecular design, which is described in "Structure based drug design", Blundell. Nature 384 suppl., 23–26 (1996).

All of these strategies focus on the design of lead compounds (drug precursors) having biological activity against a defined protein or nucleic acid target. Possible interactions of these compounds with other proteins and nucleic acids are not accounted for by these methods. These interactions have implications to secondary therapeutic effects, unwanted side effect and toxicity. Although good biological activity is a necessity, a drug candidate needs to pass additional tests and clinical trials for side effect, toxicity, bioavailability as well as efficacy. These tests and clinical trials are very costly and time consuming.

Computer methods and apparatus for identifying protein and nucleic acid targets can facilitate fast-speed predictions of drug-protein and drug-nucleic acid interactions that might have implications for possible side effects, toxicity and other unwanted effects without costly and time-consuming tests and clinical trials. This is particularly important given that much of the $350 million and 12 years spent on average for commercial drugs have been squandered on many drug candidates that failed to ever reach the market. Surveys of drug discovery costs and times can be found in "Strategic choices facing the pharmaceutical industry: A case for innovation", J. Drews, Drug. Discov. Today 2, 72–78 (1997); "New drug development in the United States from 1963 to 1990", J. A. DiMasi, N. R. Bryant, and L. Lasagna, Clin Pharmacol Ther. 50, 471–486 (1991).

The molecular targets of a number of natural product drugs, particularly those from traditional medicinal plants, are unknown. This hinders the effort to design new drugs based on the molecular mechanism of these drugs. Experimental determination of molecular targets of a natural product is often slow and costly. However, a computer method for drug target identification would offer a fast and low cost approach to search possible drug targets.

Feasibility of Computer Drug Target Identification

A computer drug target identification strategy is feasible if: (1) a sufficiently diverse set of protein and nucleic acid 3D structures is available, and (2) a sufficiently fast and accurate drug identification algorithm is available under currently available and affordable computer systems. Prediction of therapeutic effects, side effects and toxicity requires knowledge of protein functions. As explained below, these conditions are being met.

At present, the 3D structure of 11,346 proteins, 557 protein/nucleic acid complexes and 857 nucleic acids have been released in the Protein Databank (PDB), and the number increases at a rate of more than 100 per month, as described in PDB home page http://www.rcsb.org/pdb/. About 17% of the proteins in PDB have unique sequences, as described in "Bridging the protein sequence structure gap by structure predictions", B. Rost, C. Sander. Annu Rev Biophys Biomol Struct 25, 113–136 (1996). Thus, the number of proteins has reached a meaningful level to cover therapeutic, metabolic, side effect, and toxicity targets. The introduction of high-throughput analysis methods is expected to enable the determination of 10,000 proteins with unique sequence within 5 years, as discussed in "100,000 protein structures for the biologist". A Sali, Nat Struct Biol. 5, 1029–1032 (1998).

Thus, a sufficiently diverse set of proteins and nucleic acids in PDB is expected in a few years. New advances in functional genomics and proteomics is providing information useful for predicting therapeutic effects, side effects and toxicity. Functional genomics is described in "Functional genomics: It's all how you read it", P. Hieter and M. Boguski, Science 278, 601–602 (1997). Proteomics is described in "Proteomics. An ambitious drug development platform attempts to link gene sequence to expressed phenotype under various physiological states". A. Persidis. Nature Biotech. 16, 393–394 (1998).

All drugs appear to bind to cavities of proteins or nucleic acids. Thus, a biomolecular cavity database can be introduced to facilitate computer drug target identification. A method is disclosed for computer automated generation of a biomolecular cavity database from entries of a biomolecule 3D structure database. This database can include all proteins and nucleic acids in PDB and it contains information about geometric and chemical features of cavities along with the 3D structure and chemical properties of the host biomolecules.

High-speed drug target identification can be achieved by a disclosed flexible ligand-biomolecule inverse docking algorithm. This algorithm searches a biomolecular cavity database to find proteins and nucleic acids to which a given drug or ligand can bind or weakly bind to. Testing results show that the average CPU time is 14–20 days for searching a cavity database containing a few thousands of proteins and nucleic acids.

Existing Computer Methods are not Capable of Drug Target Identification

Existing ligand-protein docking algorithms are useful only to cavities of a limited size. Human intervention is generally required to locate binding site or to derive a reduced model of a large cavity. Thus it is impractical to use existing method for automated docking of a drug to an arbitrarily chosen protein or nucleic acid in a database. For comparison, the disclosed vector-vector matching algorithm is capable of dealing with cavities significantly larger than that of existing methods.

Moreover, existing methods for generating protein cavity profiles are not suitable for development of a biomolecular cavity database. These methods normally require human intervention to either locate a binding site or to generate a specific cavity profile, which makes it impractical to generate cavity profiles for thousands of proteins and nucleic acids.

Existing methods are described in "Structure-based strategies for drug design and discovery", I. D., Kuntz, Science 257, 1078–1082 (1992); "Hammerhead: Fast, fully automated docking of flexible ligands to protein binding sites", W. Welch, J. Ruppert, and A. N. Jain. Chem. Biol. 3, 449–462 (1996); "Characterization of receptors with a new negative image: Use in molecular docking and lead optimization", C. M. Oshiro, and I. D. Kuntz. Proteins Struct. Func. Genet. 30, 311–336 (1998).

Potential Applications of the Disclosed Computer Drug Target Identification Method The disclosed methods provide a unique mechanism for fast and low cost computer identification of proteins and nucleic acids that a drug can bind to. Subsequent analysis of the function of the identified proteins and nucleic acids, coupled by the consideration of feasibility of drug delivery to site of action, can then facilitate the prediction of unknown targets, secondary therapeutic targets, possible side effects and toxicity. Thus, the invention has potential applications in:

Facilitating the determination of unknown molecular mechanisms of drugs (such as natural products).

Facilitating the determination of secondary therapeutic effects of drugs and drug lead compounds.

Facilitating the prediction of possible unwanted side effect and toxicity of drug lead compounds in early stage of drug development.

Given on-going rapid advances in structural and functional genomics, information for an increasingly diverse set of proteins and nucleic acids is becoming available. The disclosed method likely will find wider and wider application in drug design.

It is an object of this invention to provide a new method for automated computer identification of possible protein and nucleic acid targets of drugs.

It is a further object of this invention to provide a new algorithm for docking a ligand to a cavity of a protein or nucleic acid.

It is a further object of this invention to provide a new method for automated computer generation of a biomolecular cavity database from entries of a biomolecule 3D structure database.

This invention relates to a method for identifying protein or nucleic acid targets of a drug by means of ligand-biomolecule inverse docking strategy. This strategy performs successive docking of a ligand in single or multiple conformations to multiple protein and nucleic acid entries in a biomolecular cavity database by the vector-vector matching algorithm described below. If a particular conformation of the ligand can be fitted to a cavity (steric clash is allowed at this stage), an energy minimization is conducted to release possible steric clash and to optimize the conformation of the drug and that of the side chain of amino acids or nucleotides at the binding site. Energy minimization is conducted by using published algorithms and parameters similar to that used in the software AMBER. AMBER stands for Assisted Model Building with Energy Refinement and it is a package developed by researchers at University of California San Francisco. A reference for AMBER can be found in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995). Docking evaluation is performed by examination of ligand-biomolecule interaction energy computed from molecular mechanics energy functions and parameters similar to that given in AMBER. Modification is made to replace AMBER hydrogen bond function by a Morse potential function. Morse potential function has been shown to give fairly accurate hydrogen bond energy in biomolecular systems, and the use of this potential helps to save computing time considerably. Application of Morse potential function in biomolecules is described in "Premelting base pair opening probability and drug binding constant of a daunomycin—Poly d(GCAT)-Poly d(ATGC) complex", Y. Z. Chen and E. W. Prohofsky, Biophys. J. 66, 820 (1994). Proteins and nucleic acids are selected as molecular targets of the ligand if the interaction energy is below a certain value, which is a function of the number of non-hydrogen atoms in the drug.

Ligand binding is competitive in nature. A drug is unlikely to be effective if its binding is non-competitive against natural ligands and, to some extent, other drugs that bind to the same receptor site. This binding competitiveness may be partially taken into consideration for those cavities known to be ligand bound in at least one PDB entry. In addition to scoring based on the above energy threshold, computed energy is required to be comparable to that of the corresponding PDB ligand in selecting putative protein targets. Ligand-protein interaction energy for ligands found in PDB entries can be pre-computed and enclosed in a biomolecular cavity database (method described as a further aspect of this invention below).

In a further aspect of this invention, a vector-vector matching algorithm is introduced to efficiently place a ligand in a particular conformation into a cavity in a biomolecule. A ligand is composed of a group of atoms, and a cluster of spheres that fill in a cavity represents that cavity. A vector represents the relative position (distance and orientation) of an atom or a sphere with respect to the origin of a reference coordinate system on the ligand or that of sphere cluster respectively. In one embodiment, a coordinate system is defined for a ligand in a particular conformation based on three atoms of largest separation. Then, sets of three spheres matching the position of these three atoms are selected to define corresponding coordinate systems in a sphere group. Atom and sphere positions as vectors (xyz-coordinates) in the respective new coordinate systems can then be directly compared to dock a molecule into a cavity. The algorithm matches a ligand to a cavity by comparison of each of the ligand vectors with sphere vectors. A ligand is considered to be successfully placed into a cavity if each of all ligand vectors matches to at least one sphere vector.

In a further aspect of this invention, a method is introduced for computer automated generation of a biomolecular cavity database from entries of a protein or nucleic acid 3D structure database. This cavity database contains two sets of entries. The first set consists of cavity entries containing information about geometric and chemical features of cavities. The second set consists of host entries containing information about the 3D structure and chemical properties of host biomolecule. The minimum required information for each cavity entry: (1) position and radius of spheres of a sphere cluster representing a cavity, (2) spheres less than 3.5A away from a hydrogen bond donor or acceptor atom of the host biomolecule, and (3) the extent each sphere is covered by atoms of the host biomolecule. The minimum required information for each host biomolecule entry: (1) positions of atoms, (2) hydrogen bond donor and acceptors, (3) partial electrostatic charges of atoms, and (4) Van der Waals parameters. Van der Waals parameters describe the property of steric interaction of atoms. These parameters and partial electrostatic charges are described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995).

In one embodiment of the invention, each cavity entry is generated from the following procedure: (1) Computation of molecular surface of a protein or nucleic acid by using, for example, a custom designed computer program or the DMS of the software suite Midus Plus. (2) Generation of sphere groups covering cavities and surfaces of the protein or nucleic acid by using, for example, a custom designed computer program or SPHGEN of the DOCK suit of software. (3) Selection of sphere clusters, each inside a cavity. (4) Output positions and chemical properties (such as hydrogen bonding site, polar or non-polar site etc) of the selected cavity clusters. The preferred output format is that compatible to SPHGEN and CLUSTER output format. Midus Plus is described in "An Affordable Approach to Interactive Desktop Molecular Modeling,", T. E. Ferrin, et. al. J. Mol. Graphics, 9, 27–32,37–38 (1991). SPHGEN is described in "Using shape complementarity as an initial screen in designing ligands for a receptor binding site of known three-dimensional structure", R. L. DesJarlais et. al, J. Med. Chem. 31, 722–729 (1988). CLUSTER is described at DOCK web-page: http://www.cmpharm.ucsf.edu/kuntz/dock.html.

Each host entry is generated from the following procedure: (1) Determining hydrogen bond donors and acceptors. (2) Assigning to each atom AMBER partial electrostatic charges, Van der Waals parameters. (3) Assigning to each atom atomic solvation parameters. (4) Outputting the quantities, with the preferred output format being compatible to the PDB format. Atomic solvation parameters measure the solvation effect of atoms and they are described in "Solvation energy in protein folding and binding". D. Eisenberg and A. D. Mclachlan. Nature 319, 199–203 (1986).

In a further aspect of this invention, to facilitate fast-speed scoring of binding competitiveness against other ligands that bind to the same receptor site, ligand-protein interaction energy for ligand found in each cavity entry is pre-computed and enclosed in the protein cavity database. The preferred method for computing ligand-protein interaction energy for PDB ligands is that composed of molecular mechanics energy functions and parameters similar in that given in AMBER. Modification is made to replace AMBER hydrogen bond function by a Morse potential function.

DETAILED DESCRIPTION

Figure 1B:
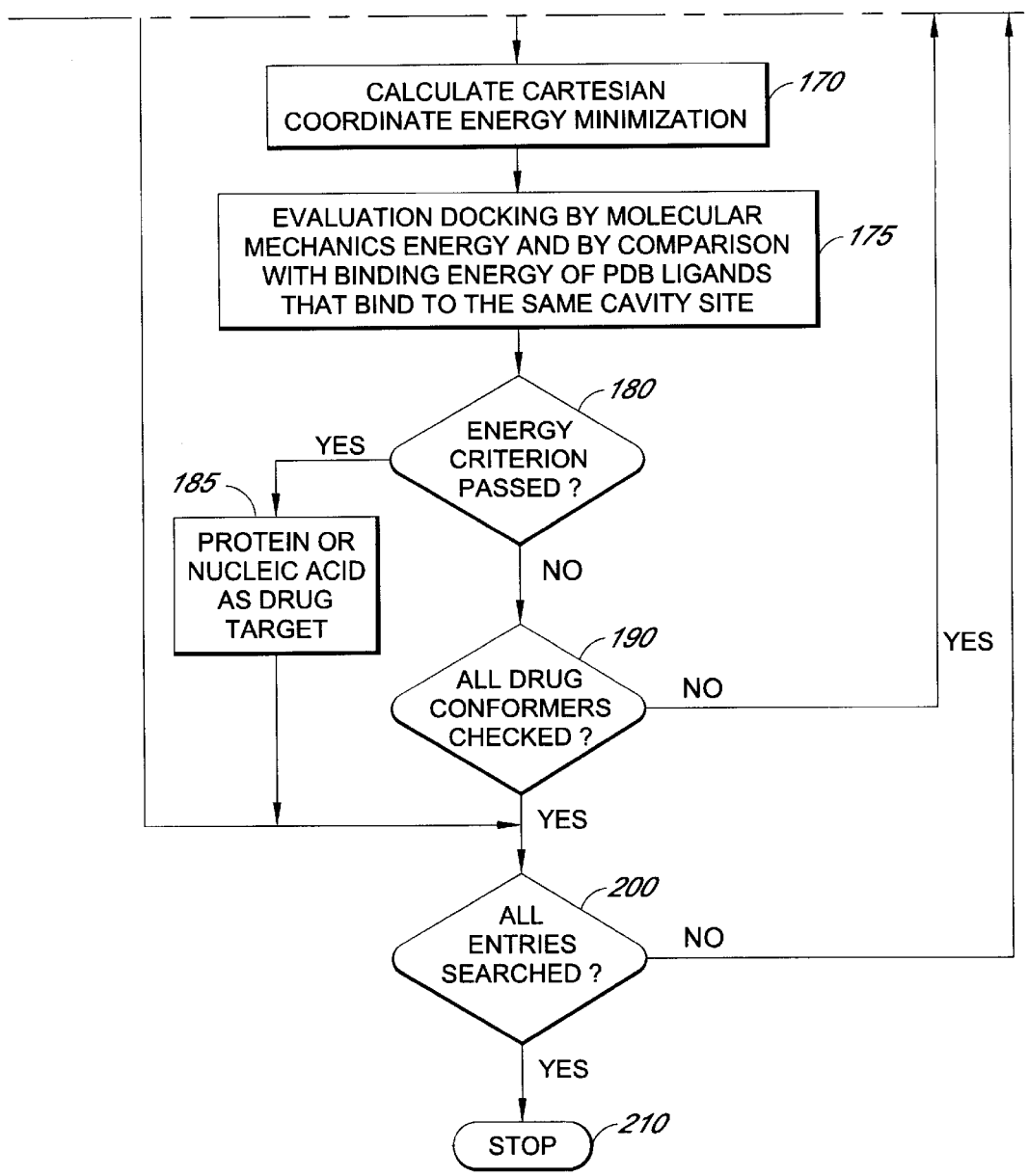
FIG. 1 is a flow diagram that illustrates one embodiment of a process for determining the possible protein and nucleic acid targets of a particular drug molecule.

This invention is implemented in an illustrative embodiment of this invention by a plurality of computer programs and a biomolecular cavity database, which are loaded into and executed on one or more computers. Illustratively, the computer may take the form of a computer workstation such as a SGI Octane R10000, an IBM compatible PC (both Windows and Linux platforms), or other similar computer system.

This invention provides a fast and low cost method for identifying possible protein and nucleic acid targets of a given drug. It has particular application in drug design. It provides a potentially useful means to facilitate fast and cost efficient prediction of side effect, toxicity and secondary therapeutic effects of a lead compound in early stage of development.

Definitions

1. Instructions

Instructions refer to computer-implemented steps for processing information in the system. Instructions can be implemented in software, firmware or hardware and include any type of programmed step undertaken by modules of the electronic financing system.

2. LAN

One example of the Local Area Network may be a corporate computing network, including access to the Internet, to which computers and computing devices comprising the financing system are connected. In one embodiment, the LAN conforms to the Transmission Control Protocol/Internet Protocol (TCP/IP) industry standard. In alternative embodiments, the LAN may conform to other network standards, including, but not limited to, the International Standards Organization's Open Systems Interconnection, IBM's SNA, Novell's Netware, and Banyan VINES.

3. Microprocessor

The microprocessor may be any conventional general purpose single- or multi-chip microprocessor such as a Pentium® processor, a Pentium® Pro processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

4. Modules

The system is comprised of various modules as discussed in detail below. As can be appreciated by one of ordinary skill in the art, each of the modules comprise various sub-routines, procedures, definitional statements, and macros. Each of the modules are typically separately compiled and linked into a single executable program. Therefore, the following description of each of the modules is used for convenience to describe the functionality of the system. Thus, the processes that are undergone by each of the modules may be arbitrarily redistributed to one of the other modules, combined together in a single module, or made available in, for example, a shareable dynamic link library.

5. Networks

The system may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

6. Operating Systems

The system may be used in connection with various operating systems such as: UNIX, Disk Operating System (DOS), OS/2, Windows 3.X, Windows 95, Windows 98, and Windows NT.

7. Programming Languages

The system may be written in any programming language such as C, C++, BASIC, Pascal, Java, and FORTRAN and ran under the well-known operating system. C, C++, BASIC, Pascal, Java, and FORTRAN are industry standard programming languages for which many commercial compilers can be used to create executable code.

8. Transmission Control Protocol

Transmission Control Protocol (TCP) is a transport layer protocol used to provide a reliable, connection-oriented, transport layer link among computer systems. The network layer provides services to the transport layer. Using a two-way handshaking scheme, TCP provides the mechanism for establishing, maintaining, and terminating logical connections among computer systems. TCP transport layer uses IP as its network layer protocol. Additionally, TCP provides protocol ports to distinguish multiple programs executing on a single device by including the destination and source port number with each message. TCP performs functions such as transmission of byte streams, data flow definitions, data acknowledgments, lost or corrupt data re-transmissions, and multiplexing multiple connections through a single network connection. Finally, TCP is responsible for encapsulating information into a datagram structure.

Overview

One embodiment of the invention is a method for identifying possible protein and nucleic acid targets of a drug through an automated ligand-biomolecule inverse docking procedure. A ligand is a small molecule, such as a drug, that can bind to a protein or nucleic acid. A biomolecule represents a protein or nucleic acid. Docking is a process of trying to fit one or more molecules (ligands) in single or multiple conformations to a cavity in another molecule (a biomolecule). Inverse docking is a process of trying to fit a molecule (ligand) in single or multiple conformations to the cavity of one or more molecules (biomolecules).

One embodiment of the invention is a method that includes:

a) Performing successive inverse docking of a ligand in single or multiple conformations to each protein or nucleic acid entry in a biomolecular cavity database. A vector-vector matching algorithm is disclosed as the preferred method for docking. A method is also disclosed for generating a biomolecular cavity database from entries of a protein or nucleic acid 3D structure database.

b) Releasing possible steric clash and optimizing the conformation of the structure of the successfully docked entry by energy minimization on the whole ligand and the side chain of amino acids or nucleotide residues around the ligand. The preferred procedure involves two steps. First is a limited torsion space conformation search, and the second is multiple iterations of Cartesian coordinate space energy minimization for the drug and surrounding amino acid or nucleic acid residues using widely used molecular mechanics energy functions and parameters.

c) Selecting the protein or nucleic acid as a drug target if the ligand-biomolecule interaction energy is below a certain value, and, in case the cavity has a ligand in at least one PDB entry, this energy is comparable to the largest ligand-protein interaction energy of the corresponding PDB ligand. The preferred method for energy computation is that uses molecular mechanics energy functions and parameters; and d) Repetitively executing step (a) to (c) until all entries in a biomolecular cavity database are searched.

Another embodiment of the invention is a vector-vector matching algorithm for docking a ligand to a cavity of a biomolecule. A ligand is composed of a group of atoms. A cluster of spheres, which fill in a cavity, represents that cavity. A method for computer automated creation of such a cavity sphere cluster is also disclosed. A vector represents relative position (distance and orientation) of an atom or a sphere with respect to a reference point on the ligand or sphere cluster respectively. The algorithm includes the steps of:

(a) Defining the reference point and a new coordinate system for the ligand using three unique atoms (atom A, B and C). These atoms are selected such that atom A and B has largest distance and atom C has largest vertical distance to the line between atom A and B. The vector for each ligand atom is expressed by the xyz coordinates in this new coordinate system.

(b) Selecting combinations of three spheres (sphere A, B and C) from a sphere cluster such that the relative positions of these spheres match the corresponding positions of atom A, B and C of the ligand. A match is assumed to be true if the difference in position is less than 3 angstroms. The distance between two spheres is defined as that between the center of these spheres. If no such combination is found, stop the procedure.

(c) For each selected combination, define the reference point and a new coordinate system for the cluster based on the positions of the three spheres. The vector for each sphere is expressed by the xyz coordinates in this new coordinate system.

(d) Comparing ligand vectors with sphere vectors. Matching (or docking) is successful if each of all ligand vectors matches at lest one sphere vector.

(e) Repetitively executing step (c) and (d) until all selected combinations are evaluated.

Another embodiment of the invention is a method for computer automated generation of a biomolecular cavity database from entries of a protein or nucleic acid 3D structure database. This cavity database contains two sets of entries. One set includes cavity entries containing information on geometric and chemical features of cavities, and the other set includes host entries containing information on 3D structure and chemical properties of host biomolecules. The said method includes the steps of:

(a) From an entry of a biomolecule 3D structure database (preferred file format is the standard Protein Data Bank format), creating surface profile of the host biomolecule by use of, for example, a custom designed program or an existing software such as Midus Plus.

(b) From molecular surface profile, constructing spheres that fill or cover the surface of the host molecule by use of, for example, a custom designed program or an existing software such as SPHGEN in DOCK suit of software.

(c) Dividing spheres into separate groups each covering a local region of molecular surface (e.g., a cavity or a groove) by use of, for example, a custom-designed program or an existing software such as CLUSTER in DOCK suit of softwares.

(d) From each group, selecting clusters each reside within a particular cavity. Selection of a sphere in a cavity is based on its darkness value that measures the extent this sphere is covered by atoms of host biomolecule in that cavity. A sphere is considered to be inside a cavity if more than 75% of the directions of surrounding space (within a range of 15 angstrom from the sphere) is covered. Such a sphere is defined as "covered". In addition, any spheres that are within 5 angstroms of a "covered" sphere are included in that cluster. If no cluster is found, go back to step (a) and start with another entry.

(e) For each selected cavity cluster, creating a cavity entry of the biomolecular cavity database. This entry contains positions and darkness value for each sphere, and the name and chemical properties of the nearest amino acid or nucleic acid in the host biomolecule. The preferred output format is that compatible to SPHGEN and CLUSTER output format.

(f) Repetitively executing step (e) until all selected cavity clusters are processed. Then creating a host entry for the biomolecular cavity database. This entry contains xyz coordinates and other chemical parameters for each atom of the host biomolecule. The preferred output format is that compatible to PDB format; and repetitively executing step (a) to (f) until all entries in a biomolecule 3D structure database are processed.

(g) Scanning the cavity entries to check whether each cavity contains a binding ligand in the original structure. If yes, the process computes the ligand-protein interaction energy and adds it to the cavity entry.

(h) Scanning those cavity entries without a ligand in the original structure to check whether there is a ligand in the same cavity in any other entry of the same protein or nucleic acid. If yes, the process adds the largest of ligand-protein interaction energy value of the corresponding ligands to the cavity entry.

Program 1. Computer Identification of Possible Protein and Nucleic Acid Targets of a Drug Referring now to the drawings and, in particular, to FIG. 1, there is disclosed a process 100 for carrying out a method for the identification of possible protein and nucleic acid targets of a given drug molecule. Also disclosed is a vector-vector matching algorithm for determining whether a particular drug docks to a particular biomolecule. In the process 100, a drug is docked successively to every entry in a biomolecular cavity database by the procedure as described below and given in the flow chart of FIG. 1.

The process 100 begins at a state 110, wherein the 3D structure file of a drug in Brookhaven Protein Databank (PDB) or Molecular Design Limited (MDL) "Mol" file format is loaded into a computer memory. Of course, it should be realized that molecules in other formats are anticipated to function similarly.

The files that are imported into the computer memory are normally provided by external sources. For example, MDL is the company that produces a popular chemical 3D structure database (includes many drugs and other small molecules of potential therapeutic value). The MDL mol format is used for entries in that database. PDB and MDL Mol format are the most popular format for 3D structure of drugs and other small molecules.

The process 100 then moves to a sate 115 wherein the chemical properties (partial electrostatic charges, Van der Waals parameters, and solvation parameters) and information about rotatable bonds and hydrogen bond donor and acceptor sites of the drug are generated and saved into a computer file that has an extended PDB format.

This extended PDB file format is compatible to the conventional PDB file format but contains additional data relating to chemical properties. Partial electrostatic charges are taken from the AMBER reference: "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995), with additional variations to conform to the fixed total charge of the drug. Van der Waals parameters are derived from the AMBER reference: "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995). The solvation parameters that are included in the extended PDB format are derived by reference to "Solvation energy in protein folding and binding". D. Eisenberg and A. D. Mclachlan. Nature 319, 199–203 (1986).

Figure 2:
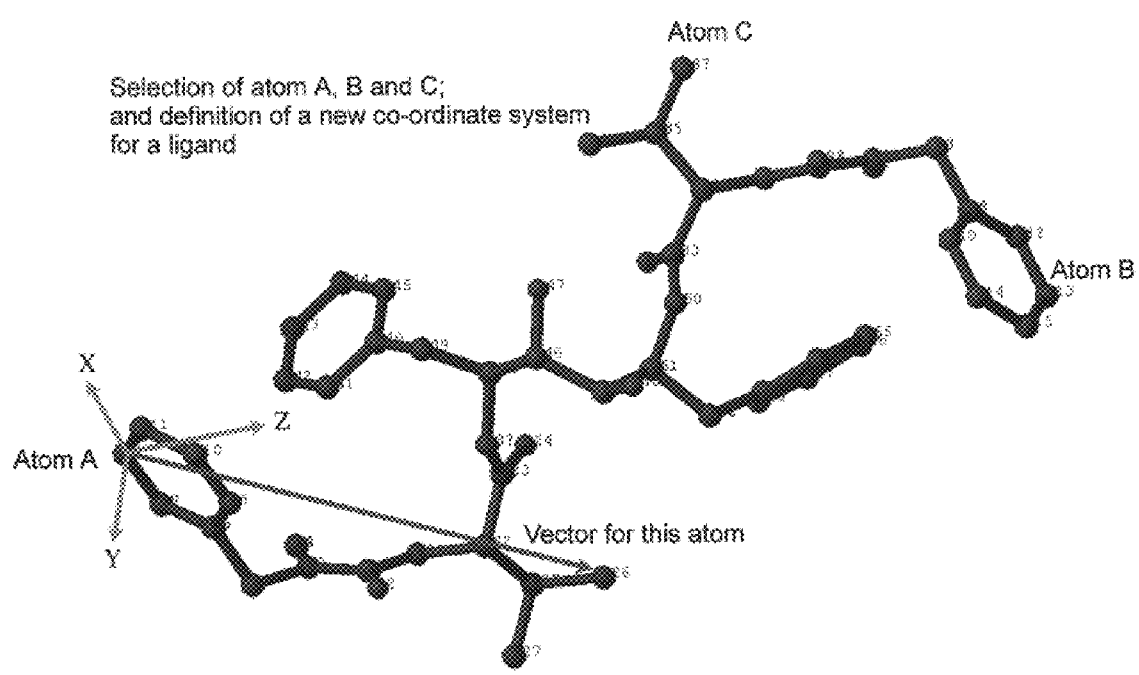
FIG. 2 is schematic diagram of an HIV-1 protease inhibitor illustrating a set of vectors X, Y and Z in a three dimensional coordinate system.

The process 100 then moves to a state 120 where in single or multiple conformation of a drug may be generated and vectors representing the relative position of atoms with respect to a chosen reference point on the drug in each conformation are generated. As illustrated in FIG. 2, three unique atoms (atom A, B and C) are used to define the reference point and a new coordinate system. These atoms are selected such that atom A and B have the largest distance from one another on the drug. The position of Atom C is chosen as the furthest vertical position on the drug from the line defined by the points A and B in three-dimensional space.

Atom A is chosen as the origin of new coordinate system (reference point). The line between atom A and B defines the z axis. The x axis is perpendicular to the plane formed by atom A, B and C. The y axis can be derived from x and z axis. The vector for each ligand atom is expressed by the xyz coordinates in this new coordinate system.

FIG. 2 illustrates atoms A, B and C together with the new xyz coordinate system for an anti-AIDS drug (HIV-1 protease inhibitor).

Referring back to FIG. 1, the process 100 then moves to a state 125 wherein a cavity entry, and the corresponding host entry, in a biomolecular cavity database is loaded from a biomolecular cavity database 130. A determination is made whether the same host biomolecule has already been selected as drug target. If the same host biomolecule has been selected, another entry is selected. If the biomolecule has not already been selected, the process 100 proceeds to the next step.

The entry that is loaded from the biomolecular cavity database contains information on the coordinate positions of spheres in a sphere cluster that fill in the cavity of a protein or nucleic acid. In addition, the cavity database contains information on the "darkness values" for each sphere, and the name and chemical properties of the nearest amino acid or nucleic acid. For each cavity that has a ligand in at least one PDB entry of the same protein, the ligand-protein interaction energy for the ligand in same cavity or that with the largest energy is also included in the corresponding cavity entry. This allows a comparison of the previously determined ligand-protein interaction energy with the interaction energy estimated between the currently selected PDB protein and the ligand.

A darkness value of a sphere is a measure of the extent that the sphere is covered by atoms of the host biomolecule. A sphere is considered to be inside a cavity if more than 75% of the direction of surrounding space (in a range of 15 angstroms from the sphere) is covered. In addition, any spheres that are within 5 angstroms of a member in cluster are included in that cluster. The host entry contains information on positions, atom types, partial electrostatic charges, Van der Waals parameters, and solvation parameters of atoms in host biomolecule. Ligand-protein interaction energy for a PDB ligand is composed of molecular mechanics energy functions and parameters similar, but not the same, as the AMBER system. Modification is made to replace AMBER hydrogen bond function by a Morse potential function. The energy function is:

$$V=\Sigma_{H\ bonds}[V_0(1-e^{-a(r-r0)})^2-V_0]+\Sigma_{non\ bonded}[A_{ij}/r_{ij}^{12}-B_{ij}/r_{ij}^6+q_iq_j/\epsilon_r r_{ij}]$$

In this function, r is hydrogen bond donor-acceptor distance; $V_0$, a and $r_0$ are hydrogen bond potential parameters and they are given in "Premelting base pair opening probability and drug binding constant of a daunomycin—Poly d(GCAT)-Poly d(ATGC) complex", Y. Z. Chen and E. W. Prohofsky, Biophys. J. 66, 820 (1994); $A_{ij}$ and $B_{ij}$ are van der Waals parameters; $\epsilon_r$ is the dielectric constant, $q_i$ and $q_{ij}$ are the partial charges of the i-th and j-th atoms, and $r_{ij}$ is the distance between them. These terms and parameters are from the united atom version of AMBER described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995).

Figure 3:
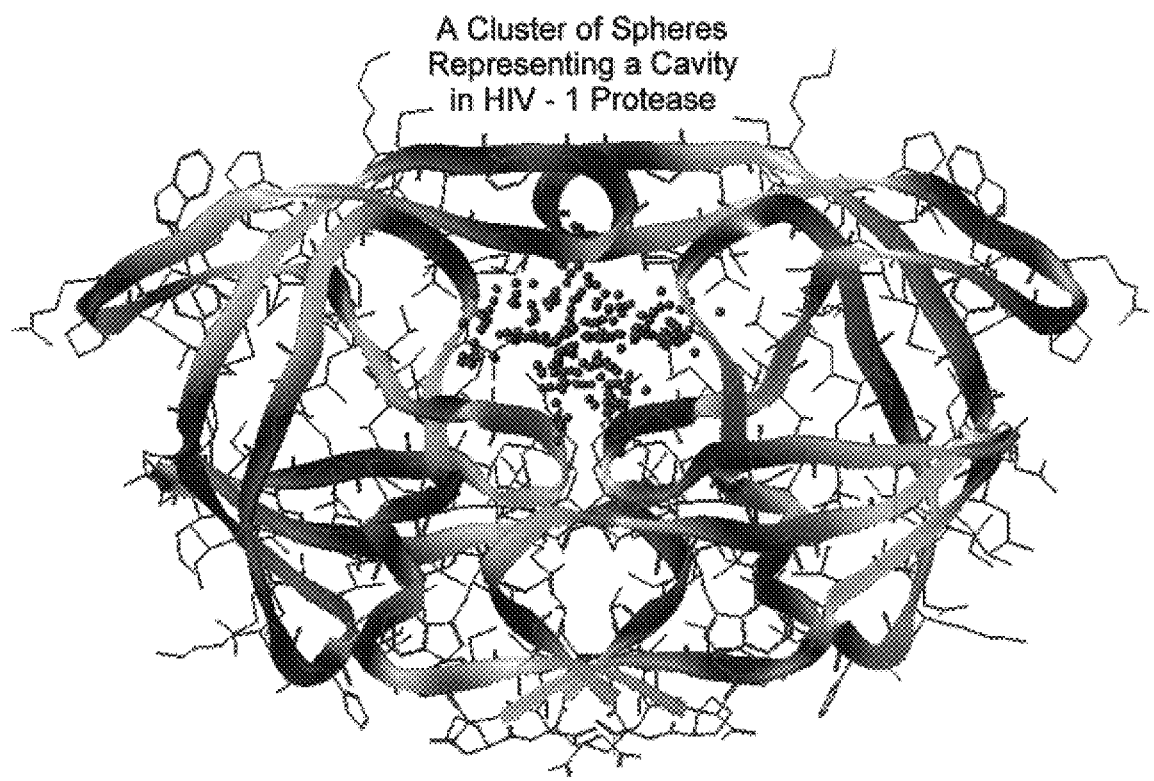
FIG. 3 is a schematic diagram of a sphere cluster in a cavity of the HIV-1 protease protein.

As one example, FIG. 3 shows a sphere cluster 135 of an HIV-1 protease protein 140.

The process 100 then moves to state 145 wherein vectors representing the relative position of each sphere to a reference point in the sphere cluster is generated. In order to calculate the relative position of each sphere in the sphere cluster, combinations of three spheres (sphere A, B and C) from the sphere cluster are selected. These three spheres are selected such that the relative positions of these spheres match the corresponding positions of atom A, B and C of the ligand. A match is assumed to be true if the difference in position is less than 3 angstroms. The distance between two spheres is defined as that between the center of these spheres.

For each selected 3-sphere combination, the three spheres are used to define the reference point and the new coordinate system. Sphere A is chosen as the origin of a new coordinate system (reference point). The line between sphere A and B defines the z axis. The x axis is chosen to be perpendicular to the plane formed by spheres A, B and C. The y axis can be derived from x and z axis. The vector for each sphere is expressed by the xyz coordinates in this new coordinate system.

If there are more than one selected 3-sphere combination, multiple sphere vector sets are generated for each cluster.

Figure 4:
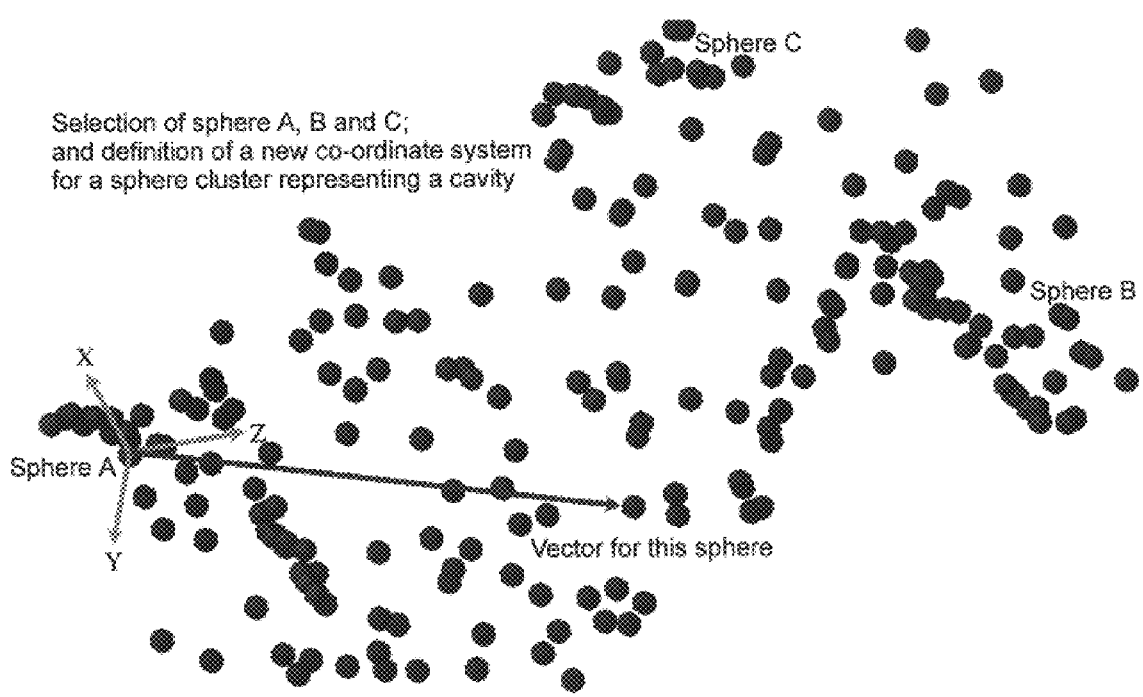
FIG. 4 is a schematic diagram of a set of spheres in a sphere cluster representing the cavity of a biomolecule.

FIG. 4 illustrates spheres A, B and C of a 3-sphere combination together with the new xyz coordinate system for the sphere cluster representing the cavity in HIV-1 protease.

The process 100 then moves to a state 150 wherein the docking of a drug in one conformation to a cavity is performed by the disclosed vector-vector matching algorithm.

Figure 5:
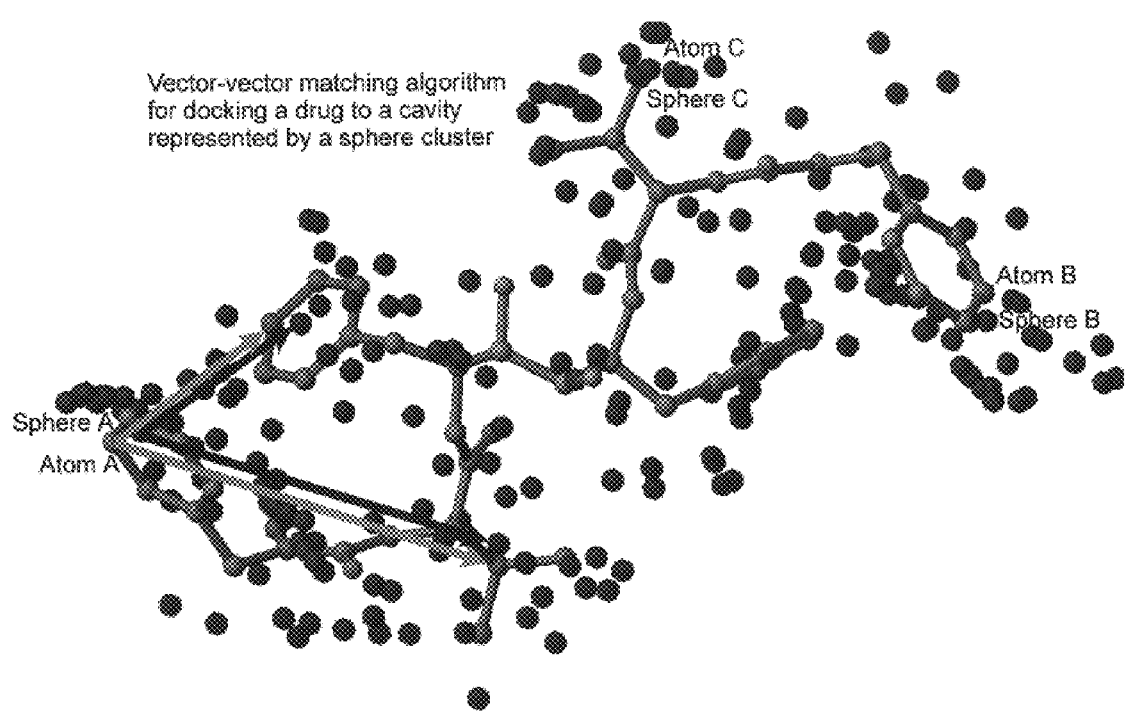
FIG. 5 is a schematic diagram of a drug (ball and stick) being matched with a sphere cluster (separate balls) using a vector-vector matching algorithm.

Drug vectors are compared to vectors in each sphere set. The comparison is made by computing the difference between the xyz coordinates of a drug vector with that of a sphere vector taken from the 3-sphere combination. A match of two vectors is assumed to be true if the difference is less than 1 angstrom. FIG. 5 illustrates the comparison of drug vectors with sphere vectors.

The process 100 then moves to a decision state 155 in order to check whether each of all vectors of the drug matches at least one vector in a sphere vector set. If no match is found for all sphere vector sets the process 100 moves to a decision state 160 to check whether or not all conformations of a drug is docked. If not, the process 100 moves to 150 to dock the next conformation. If yes, the process 100 moves to a decision state 200.

Otherwise the process moves to the next state 165. However, steric clash between the drug and host biomolecule is allowed at this stage.

At state 165 the successfully docked structure is then subjected to a limited torsion-space conformation optimization to relieve steric clash. This optimization involves a torsion grade search of −10° to +10° with 5° interval for all rotatable bonds in the drug and those of the side chain of amino acids or nucleotides within 5 angstrom of the drug. The conformation with the lowest energy value is selected as the optimized conformation. Energy is computed by the following molecular mechanics function:

$$V=\Sigma_{H\ bonds}[V_0(1-e^{-a(r-r0)})^2-V_0]+\Sigma_{non\ bonded}[A_{ij}/r_{ij}^{12}-B_{ij}/r_{ij}^6+q_iq_j/\epsilon_r r_{ij}]$$

In this function, r is hydrogen bond donor-acceptor distance; $V_0$, a and $r_0$ are hydrogen bond potential parameters and they are given in "Premelting base pair opening probability and drug binding constant of a daunomycin—Poly d(GCAT)-Poly d(ATGC) complex", Y. Z. Chen and E. W.

Prohofsky, Biophys. J. 66, 820 (1994); $A_{ij}$ and $B_{ij}$ are van der Waals parameters; $\epsilon_r$ is the dielectric constant, $q_i$ and $q_{ij}$ are the partial charges of the i-th and j-th atoms, and $r_{ij}$ is the distance between them. These terms and parameters are from the united atom version of AMBER described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995).

The process 100 then moves to a state 170 wherein fifty iterations of a Cartesian coordinate energy minimization are performed. All atoms of the drug and those of the side chain of amino acids and nucleotides within 5 angstrom of the drug are allowed to move in this minimization.

Energy minimization can be conducted by steepest decent method described in "Linear and nonlinear programming, $2^{nd}$ edition", D. G. Luenberger, Eddison-Wesley, 1984. In this method, the search direction is the derivative of the energy function at the current position. The energy function is:

$$V = \frac{1}{2} \Sigma_{bonds} K_r$$

$$(R-R_{eq})^2 + \frac{1}{2} \Sigma_{angles}$$

$$K_\theta (\theta - \theta_{eq})^2 + \frac{1}{2}$$

$$\Sigma_{torsions} V_n [1 - \cos(n(\phi -$$

$$\phi_{eq}))] + \Sigma_{H\ bonds} [V_0$$

$$(1 - e^{-a(r-r0)})^2$$

$$-V_0] + \Sigma_{non\ bonded}$$

$$[A_{ij}/r_{ij}^{12} - B_{ij}/r_{ij}^6$$

$$+ q_i q_j / \epsilon_r r_{ij}]$$

In this function, R, $\theta\theta$, and $\phi$ denotes bond length, angle and torsion angle respectively; $R_{eq}$, $\theta_{e\theta}$ and $\phi_{eq}$ are taken as bond length, angle and torsion angle in the starting structure, $K_r$=900 kcal/(mol angstrom$^2$), $K_\theta$=200 kcal/(mol gradian$^2$), $V_n$=25 kcal, and n=2; r is hydrogen bond donor-acceptor distance, and $V_0$, a and $r_0$ are hydrogen bond potential parameters and they are given in "Premelting base pair opening probability and drug binding constant of a daunomycin—Poly d(GCAT)-Poly d(ATGC) complex", Y. Z. Chen and E. W. Prohofsky, Biophys. J. 66, 820 (1994);; $A_{ij}$ and $B_{ij}$ are nonbonded van der Waals parameters; $\epsilon_r$ is the dielectric constant, $q_i$ and $q_{ij}$ are the partial charges of the i-th and j-th atoms, and $r_{ij}$ is the distance between them. These terms and parameters are from the united atom version of AMBER described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995).

The process 100 then moves to a state 175 wherein the drug-biomolecule interaction energy is then computed and evaluated by using the following molecular mechanics energy function:

$$V = \Sigma_{H\ bonds}[V_0(1-e^{-a(r-r0)})^2 - V_0] + \Sigma_{non\ bonded}[A_{ij}/r_{ij}^{12} - B_{ij}/r_{ij}^6 + q_i q_j / \epsilon_r r_{ij}] + \Sigma_{atoms} \Delta \sigma_i A_{ij}.$$

In this function, r is hydrogen bond donor-acceptor distance; $V_0$, a and $r_0$ are hydrogen bond potential parameters and they are given in "Premelting base pair opening probability and drug binding constant of a daunomycin—Poly d(GCAT)-Poly d(ATGC) complex", Y. Z. Chen and E. W. Prohofsky, Biophys. J. 66, 820 (1994); $A_{ij}$ and $B_{ij}$ are van der Waals parameters; 6, is the dielectric constant, $q_i$ and $q_{ij}$ are the partial charges of the i-th and j-th atoms, and $r_{ij}$ is the distance between them. These terms and parameters are from the united atom version of AMBER described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995); $\Delta\sigma_1$ is atomic solvation parameter given in "Solvation energy in protein folding and binding". D. Eisenberg and A. D. Mclachlan. Nature 319, 199–203 (1986); and $A_i$ is the computed solvent-accessible surface area of the i-th atom.

The process 100 then moves to a decision state 180 wherein a determination is made whether the selected energy criterion is met. The docked protein or nucleic acid in a particular conformation is selected as a possible drug target at state 185 if the computed drug-biomolecule energy is below -aN-bN$^2$-cN$^3$-d kcal/mol and it is comparable to that of the corresponding PDB ligand in the cavity. The process 100 then moves to the decision state 200. Here N is the number of non-hydrogen atoms in the drug. In addition, a, b, c, and d are parameters statistically fitted to the ligand-protein interaction energy of a few dozen PDB ligands with various number of atoms. The ligand-protein structure of these PDB ligands is from the Protein Data Bank.

Figure 6:
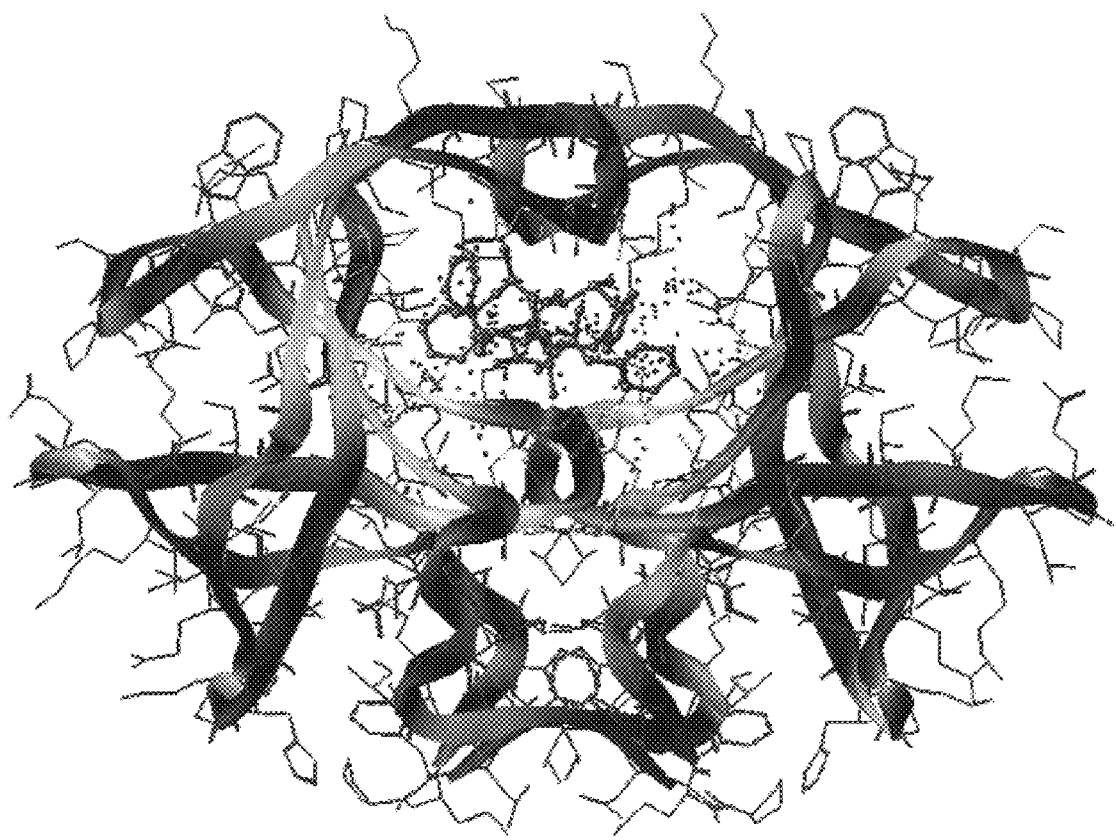
FIG. 6 is a schematic illustration of an inhibitor molecule being docked into the cavity of an HIV-1 protease molecule.

FIG. 6 shows an example of the docked structure of an inhibitor bound to HIV-1 protease. If energy criterion is not met, the process 100 moves to a decision state 190 to check whether all drug conformations are docked. If no, the process 100 moves to 150 to dock the next conformation. If yes, the process 100 moves to a decision state 200.

The process 100 at state 200 checks whether all entries in the built-in database have been searched. If all of the entries have not been searched, the process 100 returns to the state 125. However, if all of the entries have been searched, the program stops at an end state 210.

Program 2: Computer Automated Generation of a Biomolecular Cavity Database

Figure 7:
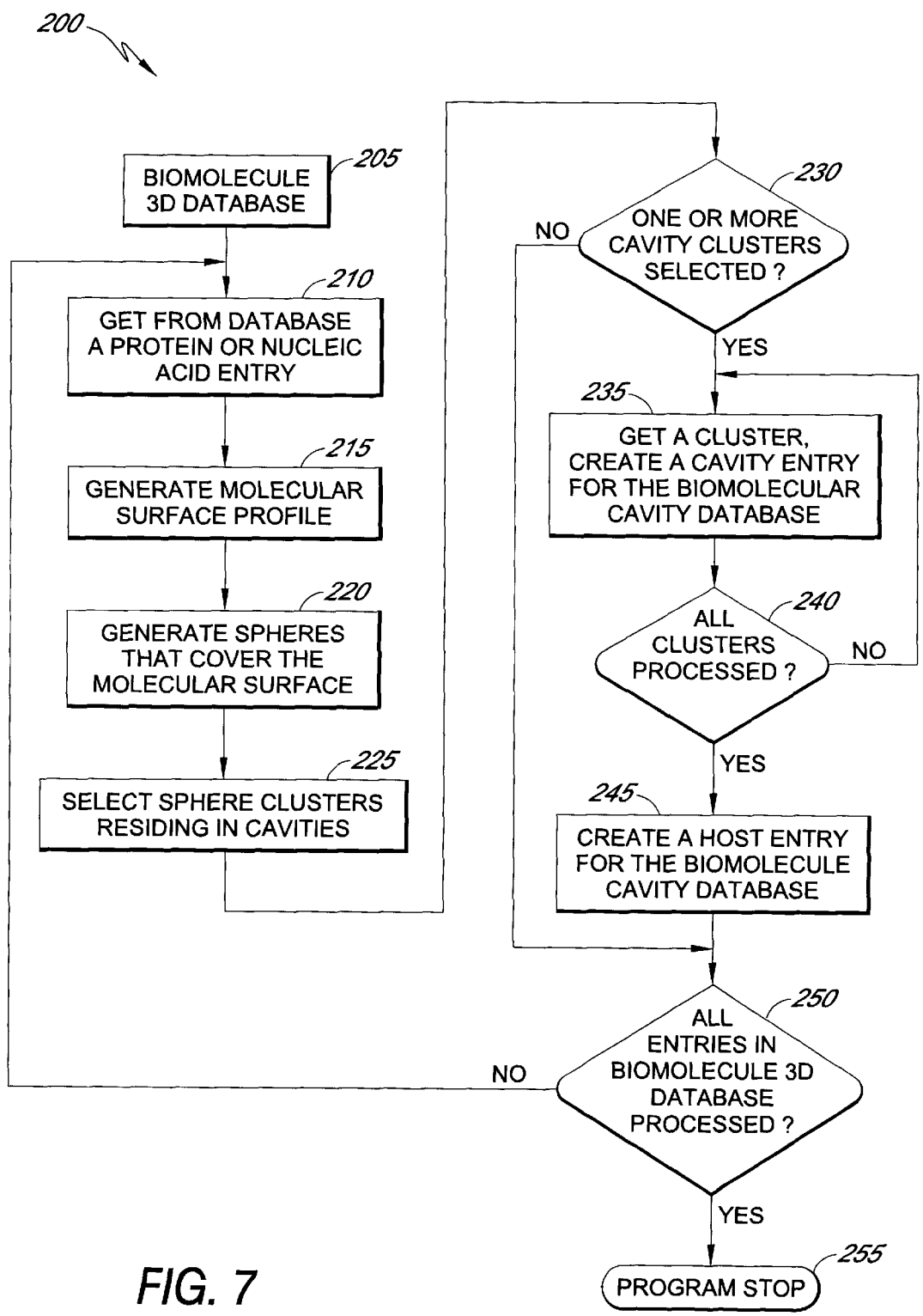
FIG. 7 is a flow diagram of an automated process for generating a biomolecular cavity database from a biomolecular three-dimensional database.

Referring now to FIG. 7, there is disclosed a process 200 for carrying out a method of generating of a biomolecular cavity database from entries of a protein or nucleic acid database. In this program, protein and nucleic acid entries from a database are successively processed by the process 200.

The process 200 is carried out as follows:

State 205: Open a protein or nucleic acid 3D structure database on a local or remote computer. Preferred file format is the PDB format.

State 210: Getting a nucleic acid or protein entry from the database. If there is a ligand, then computing the ligand-protein energy using the energy function given below. Removing any ligand and water in the structure. The energy function is:

$$V = \Sigma_{H\ bonds}[V_0(1-e^{-a(r-r0)})^2 - V_0] + \Sigma_{non\ bonded}[A_{ij}/r_{ij}^{12} - B_{ij}/r_{ij}^6 + q_i q_j / \epsilon_r r_{ij}]$$

In this function, r is the hydrogen bond donor-acceptor distance; $V_0$, a and $r_0$ are hydrogen bond potential parameters and they are given in "Premelting base pair opening probability and drug binding constant of a daunomycin— Poly d(GCAT)-Poly d(ATGC) complex", Y. Z. Chen and E. W. Prohofsky, Biophys. J. 66, 820 (1994); $A_{ij}$ and $B_{ij}$ are van der Waals parameters; $\epsilon_r$ is the dielectric constant, $q_i$ and $q_{ij}$ are the partial charges of the i-th and j-th atoms, and $r_{ij}$ is the distance between them. These terms and parameters are from the united atom version of AMBER described in "A second generation force field for the simulation of proteins and nucleic acids", Cornell, W D, Cieplak P, Bayly C I, Gould I R, Merz K M Jr, Ferguson D M, Spellmeyer D C, Fox T, Caldwell J W and Kollman P A. Journal of the American Chemical Society 117, 5179–5197 (1995).

State 215: Create a molecular surface profile of the nucleic acid or protein by use of, for example, a custom software program or an existing software program such as Midus Plus. Midus Plus is described in "An Affordable Approach to Interactive Desktop Molecular Modeling", T. E. Ferrin, et. al. J. Mol. Graphics, 9, 27–32, 37–38 (1991).

State 220: From molecular surface profile, construct spheres that fill or cover the surface by using, for example, a custom program or existing software such as SPHGEN in DOCK suit of software. SPHGEN is described in "Using shape complementarity as an initial screen in designing ligands for a receptor binding site of known three-dimensional structure", R. L. DesJarlais et. al, J. Med. Chem. 31, 722–729 (1988). The spheres are divided into separate groups, with each group covering a local region of molecular surface (e.g.:, a cavity or a groove). Software such as a custom program, or the CLUSTER program in the DOCK suit of software can be used in one embodiment. CLUSTER is described at DOCK web-page: http://www.cmpharm.ucsf.edu/kuntz/dock.html.

State 225: From each group, select clusters of spheres which reside within a particular cavity. If one or more clusters are found, go to state 235. If no cluster is found, go to state 250.

Selection of a sphere residing within a cavity is based on its darkness value that measures the extent this sphere is covered by atoms of host biomolecule in that cavity. A sphere is considered to be inside a cavity if more than 75% of the directions of the surrounding space is covered by atoms of host biomolecule. Of course, one of ordinary skill in the art could choose higher or lower percentages and be within the scope of the present invention. The darkness value is computed by scanning the surrounding space within 15 angstrom of the sphere. Its value is the portion of the directions of the surrounding space covered by host atoms multiplied by $4\pi$ (in units of solid angle). In addition, any spheres that are within 5 angstroms of a member in the cluster are included in that cluster.

State 235: For each selected cavity cluster, create a cavity entry for the biomolecular cavity database. This entry contains a position, radius, and darkness value for each sphere; spheres within 3.5 angstrom of a hydrogen bond donor or acceptor; the name and polar nature of the nearest amino acid or nucleic acid in the host biomolecule and its distance to sphere. If the selected cavity entry has a ligand in the original PDB entry, the computed ligand-protein energy is also entered. The preferred output format is that compatible to SPHGEN and CLUSTER output format.

State 240: Repetitively executing state 235 until all selected cavity clusters are processed.

State 245: Creating a host entry for the biomolecular cavity database. This entry contains xyz coordinates, partial electrostatic charge, Van der Waals parameters, and solvation parameters for each atom of the host biomolecule. The hydrogen bond donor or acceptor is also indicated. Partial electrostatic charge and Van der Waals parameters are from united atom version of AMBER described in "A new force field for molecular mechanical simulation of nucleic acids and proteins", S. J. Weiner et. Al., J. Am. Chem. Soc. 106, 765–784 (1984). Atomic solvation parameters are from "Solvation energy in protein folding and binding". D. Eisenberg and A. D. Mclachlan. Nature 319, 199–203 (1986). The preferred output format is that compatible to PDB format.

State 250: Repetitively executing the previous steps until all entries in a biomolecule 3D structure database are processed. The process 200 then ends at a State 255.

Once this process has completed, the database can be further scanned to find those cavity entries that do not have an identified ligand ("ligand-less" cavity), but there is at least one PDB entry that has identified a ligand for the same cavity of the same protein or nucleic acid. The largest ligand-protein interaction energy of the corresponding ligands is added to each of these "ligand-less" cavities.

One advantage of this embodiment of the invention over existing methods is its unique capability of finding possible protein and nucleic acid targets of a drug. In contrast, existing computer methods for ligand-protein docking is designed for screening multiple chemical compounds to find one or more compounds that can bind to a protein or nucleic acid. These existing methods are not capable of finding protein and nucleic acid targets of a drug.

This unique capability allows the methods and system disclosed herein to be used to facilitate the determination of unknown drug targets, secondary therapeutic targets, and also to facilitate the prediction of side effects and toxicity based on the analysis of the function of protein or nucleic acid targets.

The improvement of the disclosed vector-vector docking process over existing ligand-protein docking systems is in terms of computation speed and memory requirement. The disclosed vector-vector matching process only requires approximately $N^3$ rounds to complete the comparison of vectors. Here N is the larger of number of spheres in a cavity and that of a drug.

In contrast, the distance-distance programs used in the existing methods require approximately $N^4$ rounds to complete the comparison of distances. As the CPU time and memory requirement is proportional to N, our system achieves a maximum of approximately N times faster CPU time and requires approximately N times less memory. This significantly improves the computation speed and the size of cavity that the computer can manipulate.

Testing results on four protein targeting drugs have shown that the preferred embodiment of this invention correctly selected their therapeutic protein targets from 5,000 proteins in the built-in database. In addition, several proteins confirmed or implicated by experiments were also selected. A protein is said to be implicated if experimental evidence shows the protein is affected by the drug but it is not clear whether this is caused directly by drug binding to that protein. The results are summarized below:

| Drug | Therapeutic effect | No. of Human Proteins Identified | Experimental Findings | |
|---|---|---|---|---|
| | | | Confirmed | Implicated |
| 4H-Tamoxifen | Anticancer | 17 | 4 | 4 |
| Aspirin | Antiinflammation | 52 | 4 | 16 |
| Penicillin G | Antibiotic | 30 | 3 | 7 |
| Vitamin C | Supplement | 46 | 4 | 9 |
| Vitamin E | Supplement | 26 | 2 | 11 |

Another testing, the RNA targeting antibiotic drug neomycin identified 7 RNA targets, of which 3 has been confirmed and 1 implicated by experiments.

| Drug | Therapeutic effect | No. of RNAs Identified | Experimental Findings Confirmed | Implicated |
|---|---|---|---|---|
| Neomycin | Antibiotic | 7 | 3 | 1 |

Between 25% to 57% of the identified targets have been confirmed or implicated experimentally. Some of the PDB structures may be of little relevance to binding study. These include entries containing only an incomplete section or a chain, irrelevant mutants, and some macromolecular complexes. In addition, discrepancies may result from lack of consideration of gene expression patterns and pharmacokinetic and metabolic profiles of a drug. For these reasons, it is difficult to judge their performance.

The preferred embodiment of this invention can be used in identification of drug targets. The identification of addition 3D structures of proteins and nucleic acids will augment the ability of the invention still further. In addition, the development of 3D structures of additional conformations will increase the likelihood that a particular protein or nucleic acid in the database will be in the relevant conformation. Increasing the biological molecule database will also increase the ability to detect solvation effects for any particular biological molecule.

Details of some of these testing are given in the two examples given below.

EXAMPLE 1

Several compounds were tested using a preferred embodiment of the system of the present invention to determine putative binding targets. The results of these tests are provided in the table below wherein a series of ligands were tested to determine their putative binding targets in the Brookhaven Protein Database.

INVDOCK testing results for several PDB structures and on putative targets of vitamin E (RMSD stands for Root Mean Square Deviation and it is in units of angstrom. Energy is the ligand-protein interaction energy and it is in units of kcal/mol).

| Compound | Docked Protein | PDB Id | RMSD | Energy |
|---|---|---|---|---|
| Indinavir | HIV-1 Protease | 1hsg | 0.19 | −70.25 |
| Xk263 Of Dupont Merck | HIV-1 Protease | 1hvr | 0.21 | −58.07 |
| Vac | HIV-1 Protease | 4phv | 0.12 | −88.46 |
| Folate | Dihydrofolate Reductase | 1dhf | 1.24 | −46.02 |
| 5-Deazafolate | Dihydrofolate Reductase | 2dhf | 0.46 | −65.49 |
| Methotrexate | Dihydrofolate Reductase | 4dfr | 1.64 | −65.66 |
| Estrogen | Estrogen Receptor | 1a52 | 0.67 | −45.86 |
| 4-Hydroxy-tamoxifen | Estrogen Receptor | 3ert | 0.18 | −55.15 |
| Guanosine-5'-[B,G-Methylene] Triphosphate | H-Ras P21 | 121p | 0.17 | −80.2 |
| Glycyl-*L-Tyrosine | Carboxypeptidase A □ | 3cpa | 1.12 | −40.63 |
| Huperzine A | Acetylcholinesterase | 1vot | 0.93 | −39.35 |
| Aspirin | Prostaglandin H2 Synthase-1 | 1pth | 4.71 | −32.43 |
| 2'-Deoxyuridine | Thymidylate Synthase | 1syn | 0.65 | −50.89 |
| 5'-Monophosphate Vitamin E | 17□ Hydroxysteroid-Dehydrogenase | 1a27 | 0.71 | −50.01 |
| Vitamin E | Aldose Reductase | 1az1 | 0.51 | −50.44 |
| Vitamin E | Alcohol Dehydrogenase | 1dda | 0.51 | −43.92 |
| Vitamin E | Immunoglobulin | 1mcd | 3.22 | −45.83 |
| Vitamin E | Glutathione Synthetase | 2hgs | 0.54 | −41.66 |
| Vitamin E | D-Amino Acid Oxidase | 1aa8 | 0.32 | −46.87 |
| Vitamin E | Guanylyl Cyclase | 1awn | 1.51 | −40.57 |
| Vitamin E | Prostaglandin Endoperoxide Synthase | 1djj | 2.32 | −41.51 |
| Vitamin E | Nitric Oxide Synthase | 2nse | 1.13 | −41.49 |

EXAMPLE 2

Identification of Targets for the Anti-Cancer Drug Tamoxifen

The anticancer drug tamoxifen was used to test the capability of the preferred embodiment of this invention in identifying protein targets of drugs. Tomoxifen is a well-known anticancer drug and was approved as the first cancer preventive drug in 1998. Extensive research has been conducted on this drug, including a determination of its protein targets. For a review, see "Steroidal and nonsteroidal oestrogen antagonists in breast cancer: basic and clinical appraisal", R. E. Favoni, and A. d. Cupis, TiPS 19, 406–415 (1998).

Figure 8:
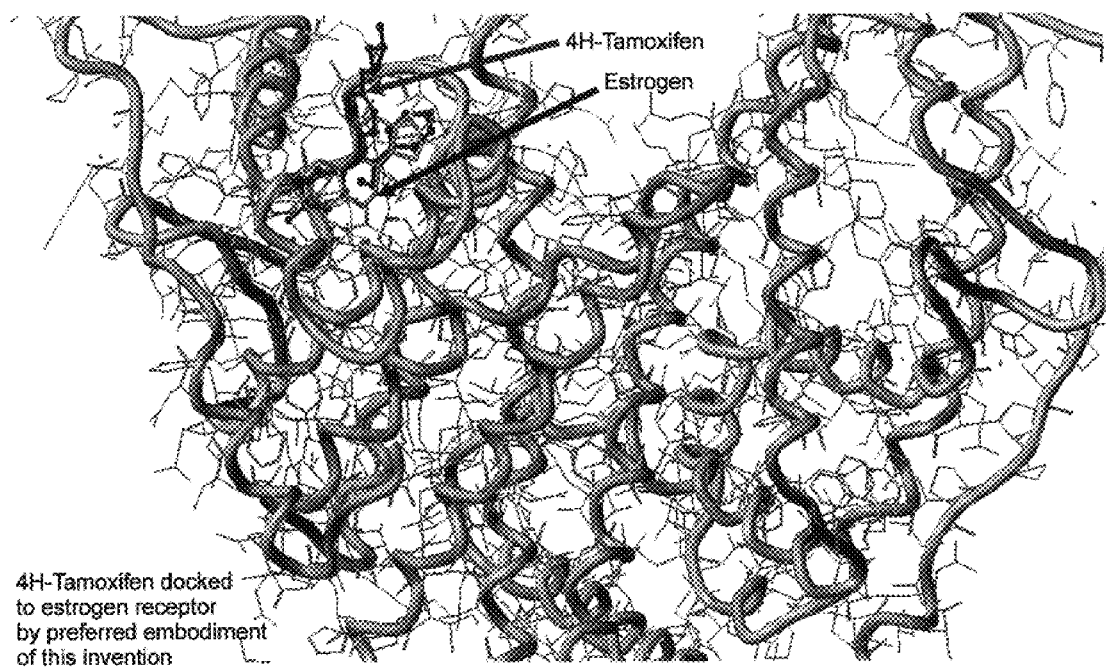
FIG. 8 is a schematic diagram of an anticancer drug 4H-tamoxifen (dark ball and stick) docked into the estrogen receptor protein (light stick structure).
Figure 9:
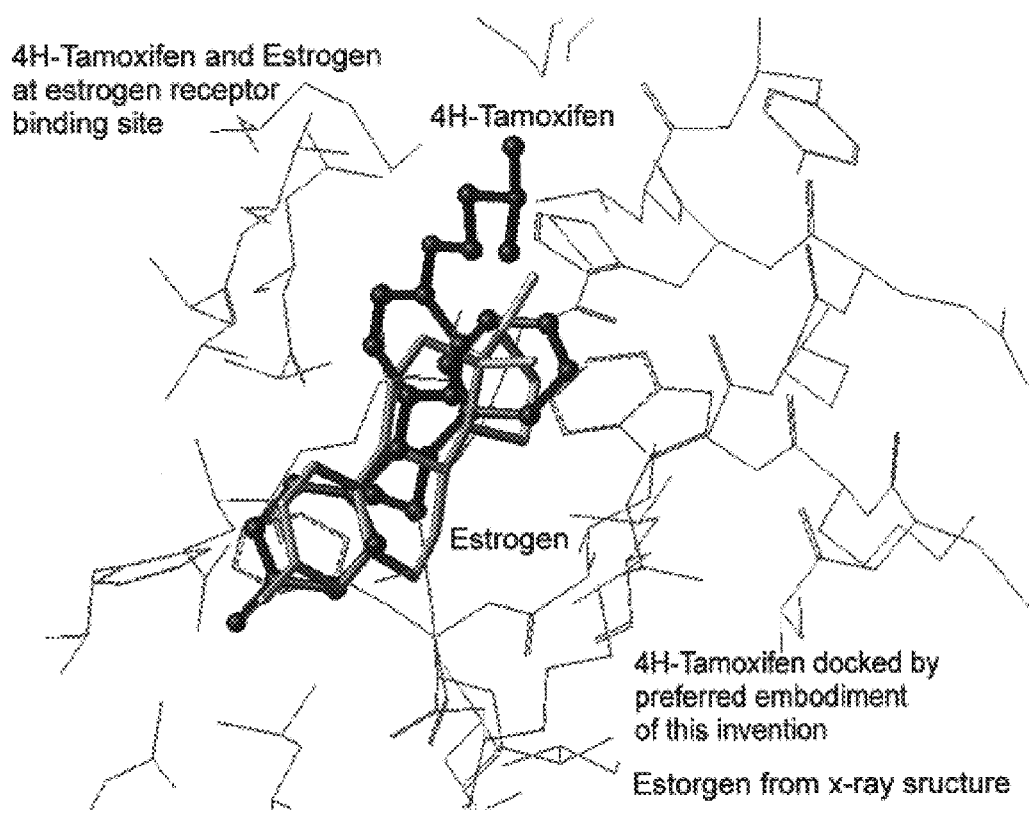
FIG. 9 is a detailed schematic diagram of the 4H-tamoxifen/estrogen binding pair from FIG. 8.

One of the known therapeutic targets of tamoxifen is the estrogen receptor. FIG. 8 shows an illustration of the structure of a tamoxifen—estrogen receptor complex generated by the preferred embodiment of this invention. For comparison, the x-ray crystal structure of natural ligand estrogen bound to this receptor is also included. Both the drug and the natural ligand bind to the same site, which is shown in FIG. 9 which validates the mechanism described herein for determining molecules that bind to drugs targets.

| Statistics of the tamoxifen search was: | | |
|---|---|---|
| Number of proteins scanned | 2,000 | (CPU time 2 weeks) |
| Number of human proteins scanned | 1,164 | |
| Number of human and equivalent protein targets identified | 17 | (4 confirmed, 4 implicated) |

A detailed list of protein targets identified by a preferred embodiment of this invention is given below together with references of relevant experimental testing:

| PDB | Protein | Experimental Finding | Target Status | Clinical Implication | Ref |
|---|---|---|---|---|---|
| 1a52 | Estrogen Receptor | Drug target | Confirmed | Treatment of breast cancer | 1 |
| 1akz | Uracil-Dna Glycosylase | | | | |
| 1az1 | Aldose Reductase | | | | |
| 1bnt | Carbonic Anhydrase | | | | |
| 1boz | Dihydrofolate Reductase | Decreased level | | Combination therapy for cancer | 2 |
| 1dht, 1fdt | 17-Hydroxysteroid Dehydrogenase | Inhibitor | Confirmed | Promotion of tumor regression | 3 |
| 1gsd, 3ljr | Glutathione Transferase A1-1, Glutathione S-Transferase | Suppressed enzyme and activity | | Genotoxicity and carcinogenicity | 4 |
| 1mch | Immunoglobulin Lambda Light Chain | Temporarily enhanced Ig level | | Modulation of immune response | 5 |
| 1p1g | Macrophage Migration Inhibitory | | | | |
| 1u1b | Purine Nucleoside Phosphorylase | | | | |
| 1zqf | Dna Polymerase Beta | | | | |
| 2n11 | Retinoic Acid Receptor | | | | |
| 1a25 | Protein Kinase C | Inhibition | Confirmed | Anticancer | 6 |
| 1aa8 | D-Amino Acid Oxidase | | | | |
| 1afs | 3-Hydroxysteroid Dehydrogenase | Effect on androgen induced activity | | Hepatic steroid metabolism | 7 |
| 1pth | Prostaglandin H2 Synthase-1 | Direct inhibition | Confirmed | Prevention of vasoconstriction | 8 |
| 1sep | Sepiapterin Reductase | | | | |
| 2toh | Tyrosine 3-Monooxygenase | | | | |

Possible Human Protein Targets of 4H-Tamoxifen identified from INVDOCK search of human and mammalian proteins.

Favoni, R. E. & Cupis, A. D. *Trends Pharmacol Sci.* 19, 406–415 (1998).

Levine, R. M., Rubalcaba, E., Lippman, M. E. & Cowan, K. H. *Cancer Res.* 45, 1644–1650 (1985).

Santner, S. J. & Santen, R. J. *J. Steroid. Biochem. Mol. Biol.* 45, 383–390 (1993).

Nuwaysir, E. F., Daggett, D. A., Jordan, V. C. & Pitot, H. C. *Cancer Res.* 56, 3704–3710 (1996).

Paavonen, T., Aronen, H., Pyrhonen, S., Hajba, A. & Andersson, L. C. *APMIS* 99, 849–853 (1991).

Rowlands, M. G. et al. *Biochem. Pharmacol.* 50, 723–726 (1995).

Lax, E. R., Rumstadt, F., Plasczyk, H., Peetz, A. & Schriefers, H. *Endocrinology* 113, 1043–1055 (1983).

Ritchie G. A. *Recent Results Cancer Res.* 71, 96–101 (1980).

EXAMPLE 2

An antibiotic drug neomycin is used to test the capability of the preferred embodiment of this invention in identifying RNA targets of drugs. Neomycin is an aminoglycocide antibiotic that inhibits bacterial protein synthesis. A number of RNA targets have been found by experimentation. Hence, this drug can be used to test the preferred embodiment of this invention. Neomycin binding to RNA is described in "Specific binding of aminoglycoside antibiotics to RNA", Y. Wang, R. R. Rando, Chem Biol 2, 281–290 (1995).

Figure 10:
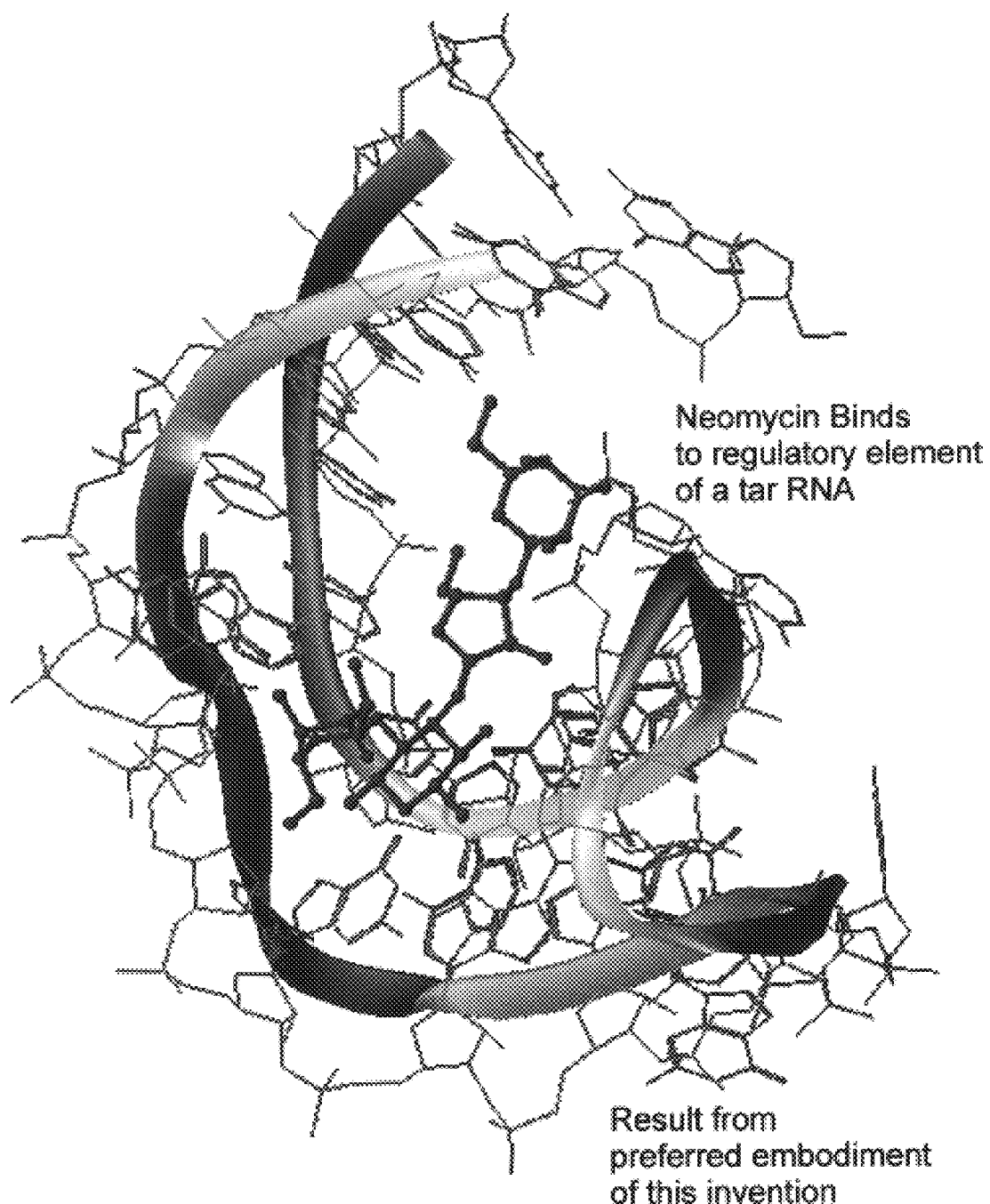
FIG. 10 is a schematic diagram of neomycin (ball and stick structure) being docked to the tar RNA of HIV-1.

Testing generated seven RNA targets for neomycin out of 195 RNA related entries in the built-in database. Three of these RNAs have been confirmed and 1 implicated by experiments. A structure of neomycin docked to regulatory element of a tar RNA is shown in FIG. 10. Statistics of the testing result are:

Number of RNAs and RNA complexes scanned: 195
Number of RNAs and RNA complexes targets identified: 7 (3 confirmed, 1 implicated)

A detailed list of RNA targets identified by a preferred embodiment of this invention is given below together with references of relevant experimental testing:

Possible RNA Targets of Antibiotic Drug Neomycin
Identified by Preferred Embodiment of This Invention

| PDB Id | RNA | Confirmed by Experiment | Implicated by Experiment | Ref. |
| --- | --- | --- | --- | --- |
| 1anr | RNA REGULATORY ELEMENT TAR | Binding | . | 1 |
| 1ago | IRON RESPONSIVE ELEMENT RNA HAIRPIN | Binding | . | 2, 3 |
| 1ebq | RNA | . | . | . |
| 1e1h | 5S RIBOSOMAL RNA | . | . | . |
| 1gid | P4-P6 RNA RIBOZYME DOMAIN | Binding | . | 4 |
| 1num | RIBONUCLEOPROTEIN/RNA COMPLEX | . | . | . |
| 1rna | RNA DUPLEX | . | Binding? | 5. |

While particular embodiments of the invention have been described in detail, it will be apparent to those skilled in the art that these embodiments are exemplary rather than limiting, and the true scope of the invention is defined by the claims that follow.

What is claimed is:

1. A method of generating an entry in a database of biomolecular cavity structures, comprising:

retrieving a three-dimensional molecular structure of a biomolecule from a biomolecular database;

generating a molecular surface profile of the molecular structure, said profile comprising a plurality of positions of surface atoms of the biomolecule;

generating a series of spheres that cover the molecular surface profile;

identifying a cavity as a cluster of spheres which are covered by a plurality of surface atoms;

identifying the coordinate positions and radii of the spheres within the cluster as a representation of the position of the cavity; and storing the positions and radii of the spheres within the cluster as the entry in the biomolecular cavity database.

2. The method of claim 1, wherein identifying a cavity comprises identifying spheres having vectors with more than 75% of their directions covered by atoms of the biomolecule.

3. The method of claim 1, further comprising identifying a darkness value for each sphere within the cluster, and storing the darkness values in the biomolecular cavity database.

4. The method of claim 1 wherein a plurality of entries in the biomolecular cavity database are stored.

5. The method of claim 1, wherein the biomolecular database comprises the Protein Data Bank (PDB).

6. The method of claim 1, wherein identifying a cavity comprises identifying first spheres within a range of 15 angstroms from said cavity.

7. The method of claim 6, wherein identifying a cavity comprises identifying second spheres within 5 angstroms of said first spheres.

8. The method of claim 1, comprising storing the name and chemical properties of a nearest amino acid in the biomolecule to the biomolecular cavity database.

9. The method of claim 1, comprising storing the name and chemical properties of a nearest nucleic acid in the biomolecule to the biomolecular cavity database.

10. The method of claim 1, comprising storing the interaction energy between a ligand and said cavity to the biomolecular cavity database.

* * * * *